United States Patent [19]
Lewis, Jr. et al.

[11] Patent Number: 5,354,305
[45] Date of Patent: Oct. 11, 1994

[54] NERVE REPAIR DEVICE

[75] Inventors: Royce C. Lewis, Jr., Lubbock, Tex.; Daniel R. Lee, Winona Lake, Ind.

[73] Assignee: United States Surgical Corporation, Norwalk, Conn.

[21] Appl. No.: 993,965

[22] Filed: Dec. 17, 1992

Related U.S. Application Data

[63] Continuation of Ser. No. 767,111, Sep. 26, 1991, abandoned.

[51] Int. Cl.⁵ ............................................. A61B 17/00
[52] U.S. Cl. .................................. 606/152; 606/151; 128/898
[58] Field of Search ......................... 606/151–153, 606/60, 72, 155, 156, 62, 67, 68; 623/13; 128/898

[56] References Cited

U.S. PATENT DOCUMENTS

| | | | |
|---|---|---|---|
| 2,136,471 | 11/1938 | Schneider | 606/62 |
| 3,123,077 | 3/1964 | Alcamo | 606/228 |
| 3,551,560 | 12/1970 | Thiele . | |
| 3,620,218 | 11/1971 | Schmitt et al. . | |
| 3,786,817 | 1/1974 | Palma . | |
| 3,809,075 | 5/1974 | Matles | 606/72 |
| 3,833,002 | 9/1974 | Palma . | |
| 3,916,905 | 11/1975 | Kuhn . | |
| 3,960,151 | 6/1976 | Kuhn . | |
| 4,169,470 | 10/1979 | Ender et al. | 606/62 |
| 4,483,339 | 11/1984 | Gillis . | |
| 4,534,349 | 8/1985 | Barrows . | |
| 4,586,504 | 5/1986 | de Medinaceli . | |
| 4,612,921 | 9/1986 | Lazo de Zbikowski | 606/72 |
| 4,662,884 | 5/1987 | Stensaas . | |
| 4,669,474 | 6/1987 | Barrows . | |
| 4,778,467 | 10/1988 | Stensaas et al. . | |
| 4,781,190 | 11/1988 | Lee | 606/139 |
| 4,804,383 | 2/1989 | Rey et al. . | |
| 4,863,668 | 9/1989 | Griffiths et al. . | |
| 4,869,242 | 9/1989 | Galluzzo . | |
| 4,870,966 | 10/1989 | Dellon et al. . | |
| 4,877,029 | 10/1989 | Valentini et al. . | |
| 4,883,618 | 11/1989 | Barrows . | |
| 4,920,962 | 5/1990 | Proulx . | |
| 4,969,909 | 11/1990 | Barouk | 606/62 |
| 4,979,956 | 12/1990 | Silvestrini | 623/13 |
| 4,986,828 | 1/1991 | de Medinaceli . | |
| 5,026,381 | 6/1991 | Li . | |
| 5,030,225 | 7/1991 | Aebischer et al. . | |
| 5,035,697 | 7/1991 | Frigg | 606/60 X |
| 5,066,296 | 11/1991 | Chapman et al. | 606/62 |
| 5,122,151 | 6/1992 | de Medinaceli . | |
| 5,147,399 | 9/1992 | Dellon et al. . | |

FOREIGN PATENT DOCUMENTS

| | | | |
|---|---|---|---|
| 0967641 | 11/1950 | France | 606/62 |
| 0576249 | 6/1976 | Sweden | 606/62 |
| 1113095 | 9/1984 | U.S.S.R. | 606/152 |

OTHER PUBLICATIONS

Jennings, Erwin R., and Cowley, R. Adams, A New Two-Way Needle for Blood Vessel Anastomosis, "Surgery", Feb. 1955, pp. 206–207.

E. R. Campion et al., *Repair of Peripheral Nerves with the Argon Laser*, The Journal of Bone and Joint Surgery, Incorporated (1990) vol. 72-A, pp. 715–723.

*Primary Examiner*—Stephen C. Pellegrino
*Assistant Examiner*—Jeffrey A. Schmidt

[57] ABSTRACT

A nerve repair device includes a resilient, elongated implant, and transverse pins for retaining the implant fixedly within the ends of the severed nerve. A sharp tip extends longitudinally from at least one end of the elongated implant, and aids in the insertion of the implant longitudinally through the ends of the severed nerve between the fascicle bundles. The severed ends are retained in close approximation for reconnection.

24 Claims, 5 Drawing Sheets

NERVE REPAIR DEVICE

This is a continuation of application Ser. No. 07/767,111 filed on Sep. 26, 1991, now abandoned.

BACKGROUND OF THE INVENTION

1. Field of the Invention

The present invention relates to medical devices for repairing injured nerves, and more particularly to a device and method for the repair of a severed peripheral nerve.

2. Discussion of the Prior Art

The repair of lacerated or severed peripheral nerves using sutures is a common surgical procedure known as neurorrhaphy. The use of this sophisticated technique in recent years has enhanced the surgeon's ability to reattach amputated body parts, to achieve composite tissue transfer, and to graft nerves. The success of such procedures is still limited because the current methods of suturing severed nerves is difficult, time-consuming, and often yields poor functional results due to a variety of factors. The replanting of amputated fingers and limbs is especially limited by poor nerve regeneration.

One such factor is the tendency of severed nerve ends to contract and pull apart after suffering damage. Consequently, when reconnection of the nerves is attempted, a tensile force may be created in the severed ends as they are drawn together, complicating both the process of rejoining the severed ends, and the healing process. In conventional surgery using a microsuture, it is difficult to retain the severed nerve ends in approximation while they are being reconnected peripherally around the epineurium with the suture. During the healing process it is also difficult to deter the tensile force created in the severed nerve ends from causing the ends to pull loose from their stitched reconnection, thus leading to poor functional reconnection of the nerve.

In one approach to promoting nerve regeneration, as disclosed in U.S. Pat. No. 4,778,467, an epineural or endoneurial monosuture is used to hold the nerve ends in close proximity, where they are enclosed by a tubular prosthesis which tightly seals the injured nerve to isolate it from the rest of the body of the host. The monosuture is formed by introducing a long needle carrying a very fine suture thread through the perineurium of the injured nerve, and drawing the monosuture and needle through the interior of the distal nerve end and into the interior of the proximal nerve end. The needle and thread are thereupon withdrawn from the proximal nerve end through the perineurium of the injured nerve. Tension applied to the monosuture brings the nerve ends into close proximity, so that the nerve ends are in contact with each other, and the ends of the monosuture are knotted. However, this device has the inherent disadvantage of preventing the surgeon from observing the anastomotic site to ascertain correct rotational alignment after enclosure of the anastomotic site with the tubular prosthesis.

Another approach seeks to protect the anastomotic site by encasing it. U.S. Pat. No. 4,883,618 shows a medical device for the sutureless repair of damaged nerves comprising longitudinally openable tubes of a body-absorbable polymer. The damaged nerve is positioned therein longitudinally without the need of suturing. The nerve purportedly becomes bonded to the porous surface of the tube so that the two portions need not be lashed together with a suture.

Another approach to sutureless tubulation involves sucking the nerve stumps into a porous metallic tube by means of a vacuum actuated instrument as disclosed in U.S. Pat. Nos. 3,916,805 and 3,960,151. However, this method risks compressive injury to the nerve upon post-surgical swelling in addition to the disadvantage of preventing the surgeon from observing the anastomotic site to ascertain correct rotational alignment.

An alternative to direct suturing is by laser fusion. Theoretical investigations into the use of an argon laser, as disclosed by E. R. Campion et al., *Repair of Peripheral Nerves with the Argon Laser*, The Journal of Bone and Joint Surgery, Incorporated (1990), have indicated in experiments involving rabbits that it is possible to allow sealing of the epineurium without thermal damage to adjacent neural tissue. However, one problem with this alternative lies in the difficulty of retaining the severed ends in close apposition while the epineurium is sealed together with the laser. Despite the progress in this area, Campion acknowledges that repair with microsuture remains the standard against which any alternative must be measured.

In the prior approaches outlined above, it is still difficult to hold the severed ends of the damaged nerve together and aligned, both during surgery and healing. Despite attempts to align proximal and distal segments of the nerve, there is a tendency for the regenerating proximal axons to sprout outside their fascicular and epineural confines. This leads to formation of neuromas and consequent incomplete reinnervation.

Thus, repairing severed nerves remains a long-standing problem that continues to plague surgeons. Despite the advances in microsurgical techniques, a patient's recovery from a serious wound is often limited by the degree of nerve damage that cannot be repaired using current technology. The present invention provides devices and methods which help to avoid the aforementioned disadvantages.

SUMMARY OF THE INVENTION

The nerve repair device in accordance with the present invention includes an elongated implant with anchor means for retaining the implant longitudinally within the ends of a severed nerve. The implant is formed of a biocompatible material, which may be resorbable, having a suitable resiliency. A sharp tip extends longitudinally from at least one end of the elongated implant and aids in the insertion of the elongated implant longitudinally into the interior of the ends of the severed nerve between the fascicle bundles or preferably just below the nerve sheath or epineurium.

As the severed ends of the nerve are urged longitudinally over the implant and anchored into close approximation with each other the anchor means retain the severed ends of the nerve in their closely approximated or abutting relationship and restrain return of the tensile force to the severed nerve ends. Consequently, the lateral width of the implant is such that the body of the implant may remain undeflected when the severed ends are urged into their closely approximated or abutting relationship.

After the implant has been inserted and anchored within the severed nerve ends, preferably by the insertion of piercing pins through the end portions of the implant, the severed ends may be reconnected by suturing, fusion or by other suitable fasteners. The anchoring means restrains the severed ends from pulling loose from their reconnection during the healing process. Thus, better nerve regeneration and healing may be promoted.

Where the implant is constructed of a material which is not resorbable, the implant may be removed after the severed nerve ends have suitably healed. To remove the implant, a longitudinal incision is made through the perineurium along the axis of the nerve to allow the non-resorbable implant to be withdrawn through the incision.

BRIEF DESCRIPTION OF THE DRAWINGS

The foregoing features of the present invention will become more readily apparent and may be understood by referring to the following detailed description of preferred embodiments of the nerve repair device and method according to the present invention, taken in conjunction with the accompanying drawings, in which.

DETAILED DESCRIPTION OF THE PREFERRED EMBODIMENTS

The invention described herein is an implant or stent device used in end-to-end anastomosis of severed peripheral nerves. The device facilitates repair and restoration of nerve function by reducing the amount of tension between the nerve ends and bringing and maintaining the severed ends in close approximation for suturing, laser or other form of surgical repair. The device also minimizes damage to nerve fibers and misalignment of nerve ends thereby advantageously reducing the proliferation of connective tissue in the anastomosis and reducing axonal outgrowth. During the healing process, the nerve repair device of the present invention acts as a splint to retain the severed nerve ends in alignment, with the tensile force created in the severed nerve ends deterred from pulling the severed nerve ends loose from their reconnection. This increased post operative stability allows greater use of the repaired body part without disrupting the nerve repair.

Figure 1:
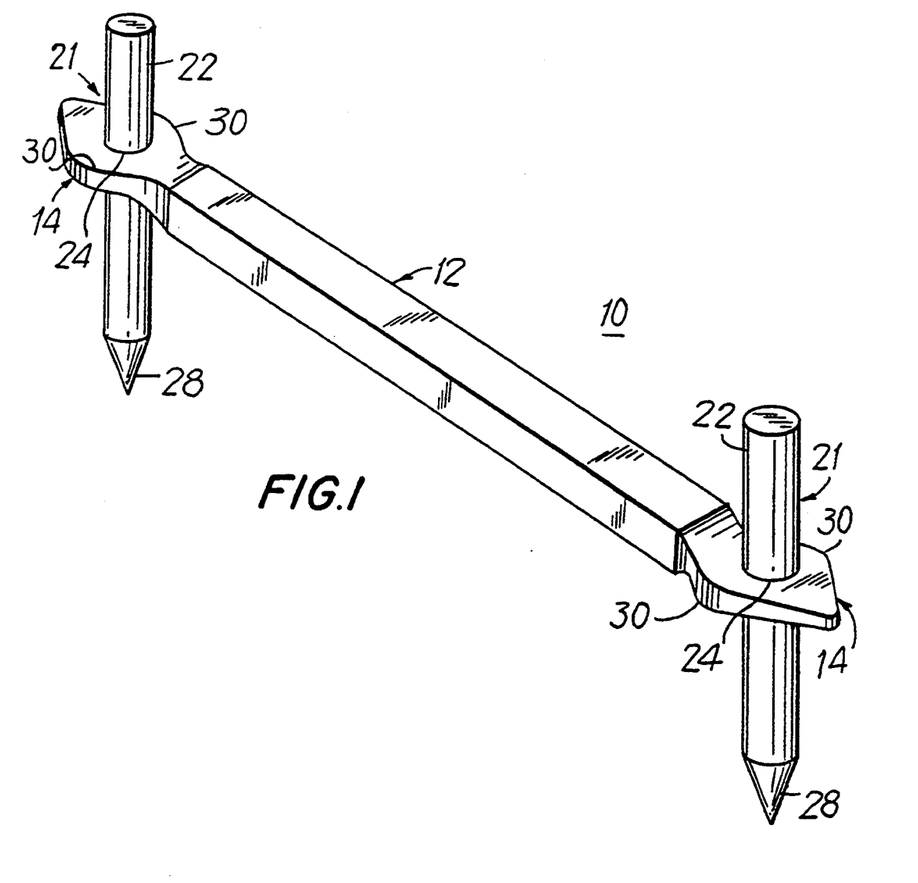
FIG. 1 is a perspective view of a preferred embodiment of the nerve repair device according to the present invention.

Referring to FIG. 1, an embodiment of the nerve repair device, shown generally at 10, comprises a narrow resilient implant 12, which is adapted to be inserted longitudinally into the ends of a severed peripheral nerve between the fascicle bundles of the nerve. To facilitate insertion into the severed ends of the nerve, a penetration tip 14, bluntly sharpened to allow passage through the nerve fascicles with a minimum of trauma to the nerves, is included at each of the ends of elongated implant 12. The longitudinal-body portion of elongated implant 12 has a flattened rectangular cross section, preferably having a width of about 0.05 inches or smaller to allow implant 12 to be more easily inserted longitudinally between the fascicle bundles. However, one skilled in the art will readily appreciate that implants of other shapes and dimensions can be used. For example, FIGS. 2 and 3 show implants having a longitudinal body portion with a circular cross section.

Implant 12 is formed from a biocompatible material which is suitably resilient to retain implant 12 in its longitudinal configuration when inserted into the severed nerve ends and positioned longitudinally therein. It can be composed of a non-resorbable material such as, for example, a surgical grade of stainless steel alloy, titanium, acrylic, polycarbonate, polyethylene, polyacetal, etc., or, alternatively, a resorbable material such as homopolymers or copolymers of lactide, glycolide, polydioxanone, trimethylene carbonate, polyethylene oxide or other suitable resorbable material or blends of these copolymers. Preferably, implant 12 is formed of a copolymer of lactide and glycolide and may be composed of a copolymer made from 18% m glycolide and 82% m lactide. If a resorbable material is utilized, the implant is left in the body not only during attachment of the nerve ends but during the healing process as well. This prolongs the ability of the device to protect the repair site from tension while healing progresses and provides increased stability.

Turning first to the embodiments of FIGS. 1-5, for example, a sharp tip extends longitudinally from at least one end of the implant of the nerve repair device. The tip may be formed by sharpening and flattening the ends of the resilient implant to facilitate penetration of the severed ends of the nerve longitudinally.

Figure 2:
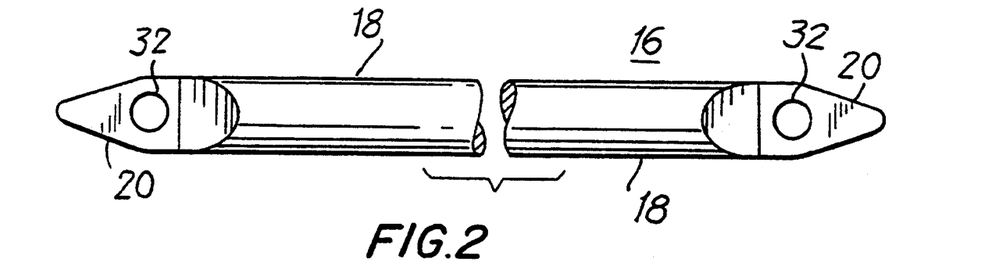
FIG. 2 is a top view of another preferred embodiment of the nerve repair device according to the present invention.
Figure 3:
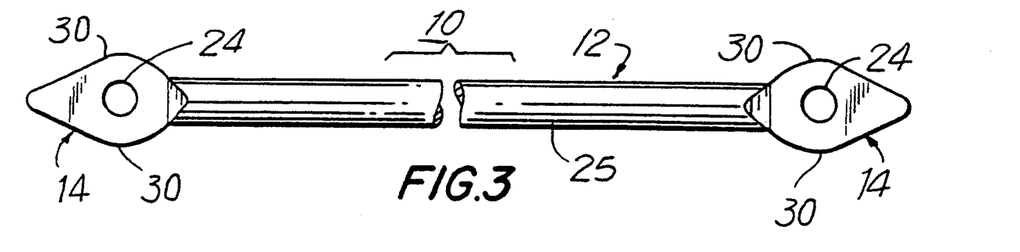
FIG. 3 is a top view of the nerve repair device of FIG. 1.
Figure 10:
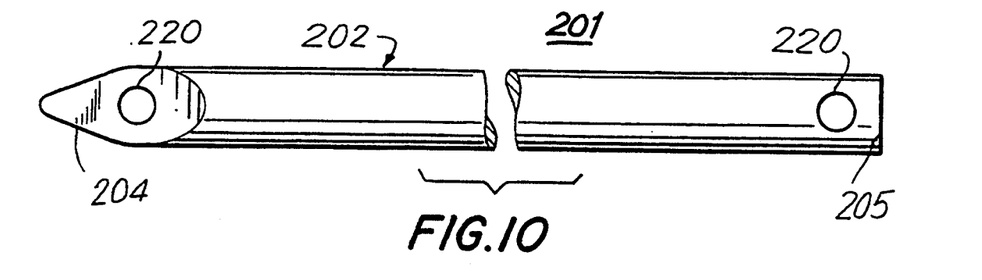
FIG. 10 is a side view of a preferred embodiment of the nerve repair device according to the present invention utilizing a single sharp tip.

In the embodiment of FIGS. 1 and 3-5, tip 14 includes opposed arcuate portions 30 that flare outward, while the embodiments of FIGS. 2 and 10 include a tip 20 with the lateral width being no wider than the width of the body of the implant.

Anchoring means 21 is provided to retain the implant longitudinally within the ends of the severed nerve, with the severed nerve ends held in close approximation for promotion of nerve growth and regeneration of nerve fibers. This close approximation also facilitates reattachment of the nerve ends by suitable means such as suturing. The anchoring means includes a pair of transverse piercing pins 22, and a pair of spaced transverse openings 24 in implant 12, with one piercing pin 22 extending axially into each opening 24. As shown, pins 22 are spaced from the ends of implant 12, transversely centered on tip 14, and positioned substantially perpendicular to implant 12. Alternatively, the pins may be positioned in different locations and angles to achieve their anchoring function.

As best seen in FIG. 3, each opening 24 may be formed by drilling through the flattened tip portion 14 of implant 12, which allows the diameter of the stem or body portion 25 of implant 12 to be minimized. Alternatively, opening 24 may be formed by eye drilling laterally through the stem of resilient implant 12 adjacent each tip 14. For non-resorbable pins, the lateral width of pin 22 and the diameter of openings 24 are suitably dimensioned to cooperate so that pins 22 may be removably retained within openings 24 for withdrawal after the nerve ends are attached. When pins 22 are in resorbable form, pins 22 may be dimensioned to lock into openings 24 so that pins 22 are retained therein until pins 22 and implant 12 are absorbed by the body. In preferred embodiments, the lateral width of pin 22 is less than about 0.05 inches, although other dimensions are possible depending on the application and the needs of the surgeon.

Figure 4:
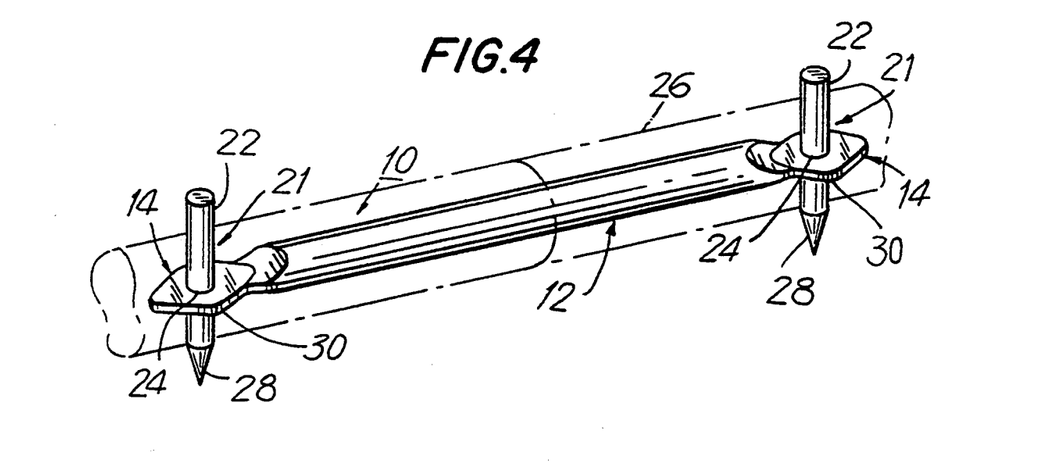
FIG. 4 is a perspective phantom view of a severed nerve joined together longitudinally by the nerve repair device of FIG. 1.
Figure 5:
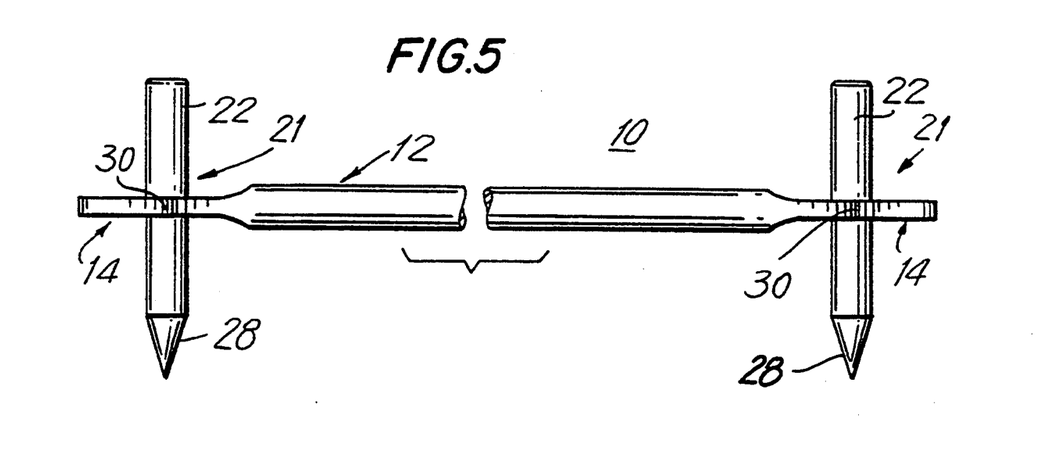
FIG. 5 is a side view of the nerve repair device of FIG. 1.

Referring to FIG. 4, piercing pins 22 extend essentially laterally through the perineurium of the nerve, indicated by phantom lines 26, and engage with implant 12 by extending axially into openings 24 to retain nerve repair device 10 within the severed ends of the nerve. In order that the piercing pins may penetrate the nerve, each piercing pin is illustratively provided with a sharp penetration tip 28 so that the pins may be inserted essentially laterally through the perineurium of the nerve into the lateral openings. Pins 22 may be formed of any resorbable material mentioned above, including a copolymer of lactide and glycolide or, if designed to be non-resorbable, of any suitable surgical grade of stainless steel alloy.

In the embodiment of FIGS. 1, 3 and 4, each end portion of the implant 12 includes protrusions that extend radially outward from the body of implant 12 to help anchor the implant. As shown, the protrusions comprise a pair of opposed arcuate portions 30 extending outwardly from opposite sides of each tip 14. When implant 12 is inserted longitudinally into the severed ends of the nerve between the fascicle bundles, arcuate portions 30 wedge laterally within the nerve to aid in retaining implant 12 fixedly in position within the severed ends of the nerve for purposes as described in detail hereafter.

In an alternate embodiment shown in FIG. 2, the end portion of tip 20 does not include the opposed arcuate portions and the width of tip 20 does not exceed the width of the body portion of the implant 12. Anchoring is accomplished in substantially the same way as in previous embodiments with piercing pins being inserted into spaced transverse openings 32 in implant 18.

Figure 12:
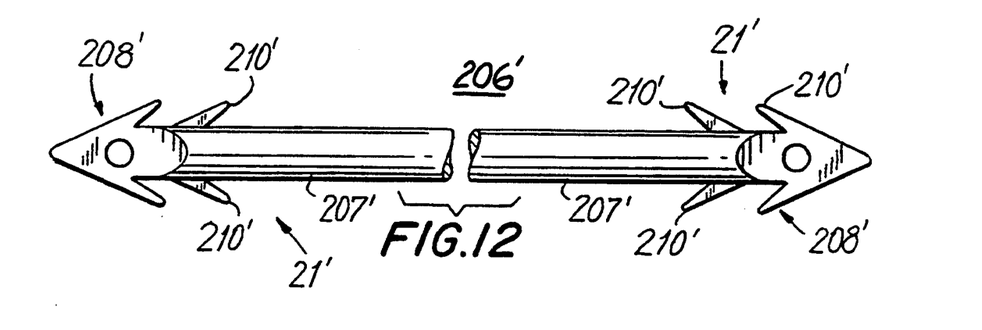
FIG. 12 is a side view of a preferred embodiment of the nerve repair device according to the present invention using projections on both ends.

In another alternate embodiment of the present invention, shown in FIG. 12, the anchoring means of nerve repair device 206' includes rearwardly facing barbed tips 208' formed integrally at each end of implant 207' that extend outwardly from the body of the implant. Each barbed tip 208' is provided with supplemental barbed portions 210' on which extend longitudinally along a portion of the length of implant 207'. Barbed portions 210' protrude at an acute angle away from the tips of implant 207' so that when the implant is inserted longitudinally into the severed ends of the nerve between the fascicle bundles, barbed portions 210' may wedge laterally within the nerve to aid in retaining the implant in position within the severed ends of the nerve.

Figure 6:
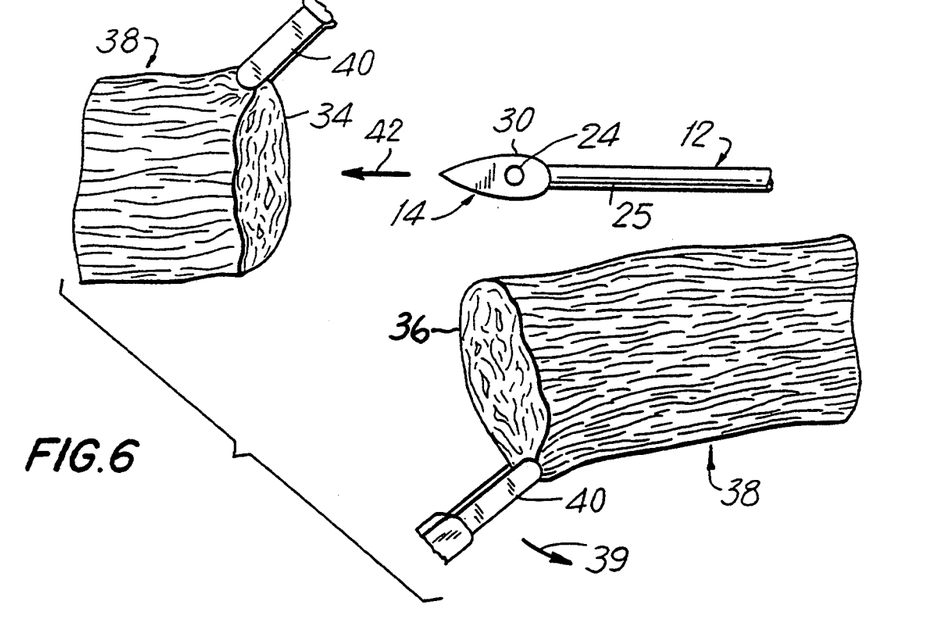
FIGS. 6-8 are perspective views showing the reapproximation and repair of severed ends using the nerve repair device of FIG. 1.
Figure 7:
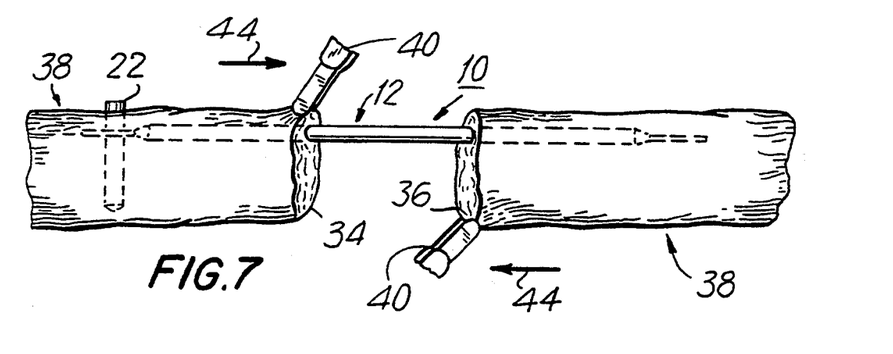
Figure 8:
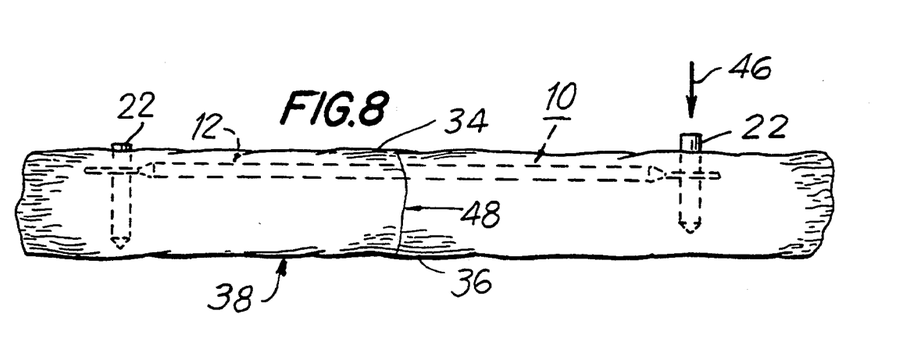

Typically, in repairing a damaged nerve, access is provided to the severed ends which typically contract and pull apart after suffering damage. When reconnection of the nerves is attempted, a tensile force may be created in the severed ends as they are drawn together, complicating both the process of rejoining the severed ends, and the healing process thereafter which overcomes these problems. Referring to FIGS. 6–8, one preferred method of nerve repair using the implant of present invention is shown. FIG. 6, ends 34, 36 of severed nerve 38 are pulled laterally apart in the direction of arrows 39, 42 by the use of an appropriate surgical instrument such as forceps 40. Implant 12 is then partially inserted longitudinally into proximal severed nerve end 34 in the direction of arrow 42 by introducing tip 14 into proximal end 34 between the fascicle bundles of the nerve, and forcing a portion of the longitudinal length of implant 12 coaxially into the severed end 34. Note that tip 14 is configured to facilitate penetration but sufficiently dull to prevent cutting or trauma to the nerve. After insertion of implant 12 into proximal nerve end 34, distal nerve end 36 is coaxially aligned with implant 12 adjacent its opposite tip 14, and a portion of this end of implant 12 is partially inserted longitudinally within distal end 36 and force to the position shown in FIG. 7.

In this position one end of implant 12 is suitably anchored within one of the severed nerve ends by inserting one of the transverse piercing pins 22 essentially laterally through the perineurium of the nerve and into opening 24 in implant 12 adjacent tip 14 which is aligned therebelow. Separated ends 34, are drawn together longitudinally over the uncovered portion of implant 12 by pulling ends 34, 36 in the direction of arrows 44 with forceps 40 until the severed ends are brought into close approximation.

Referring to FIG. 8, the remaining transverse piercing pin 22 is inserted in the direction of arrow 46 essentially laterally through the perineurium of the nerve and into the outer opening 24 in implant 12 adjacent the other tip 14, which is aligned therebelow, to retain implant 12 in position within nerve 38. As separated ends 34, 36 are drawn together into close approximation and preferably, abutting relationship the tension formed in ends 34, 36 is lessened. Pins 22 act to restrain return of the tensile force to severed nerve ends 34, 36. Consequently, the tensile force created within severed ends 34, 36 is overcome and the severed nerve ends 34, 36 are retained in their closely approximated relationship. As may be appreciated, the lateral width of implant 12 is such that body 25 of implant 12 may retain undeflected when ends 34, 36 are urged into close approximation or abutting relationship.

With the severed nerve ends 34, 36 aligned, and retained in their close approximation or abutting relationship, ends 34, 36 may be reconnected together peripherally around the perineurium of nerve 38 as at 48 by microsuture, laser or other suitable surgical fastening means known to the art. Nerve repair device 10 therefore retains the nerves in close approximation or abutting relationship while the severed nerve ends are being reconnected peripherally around the epineurium with the suture or other suitable fastening means. Furthermore, once the superficial side of the nerve has been repaired, the nerve can be quite easily turned over as a unit using the piercing pins 22 of the device as levers to turn it over. Thereafter, during the healing process, device 10 may act as a splint, retaining severed nerve ends 34, 36 in alignment, with the tensile force in the severed nerve ends overcome and deterred from pulling the severed nerve ends loose from their reconnection.

Figure 11:
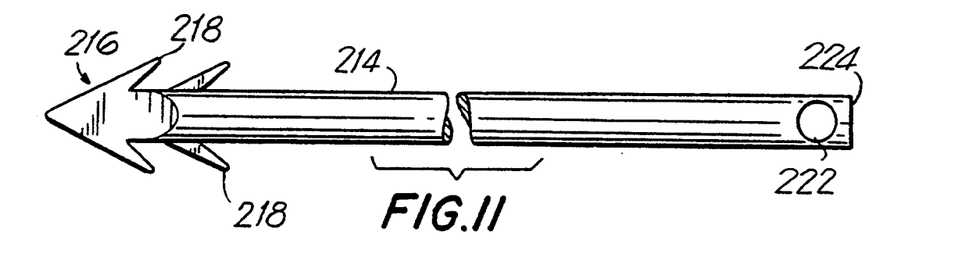
FIG. 11 is a side view of a preferred embodiment of the nerve repair device according to the present invention using projections on a single end and pins on an opposed end.

Alternate embodiments of the implant of present invention are shown in FIGS. 10, 11 and 12 which may also involve alternate methods of insertion. Referring first to FIG. 10, implant 201 has a single penetrating tip 204 and a blunt linear end 205 opposite tip 204. The implant 202 in accordance with this embodiment of the present invention includes a pair of transverse piercing pins 219, shown partially in phantom in FIG. 14 and a pair of spaced transverse openings 220, with one piercing pin being axially extendable into each opening 220, with one piercing pin being axially extendable into each opening 220. The insertion method for this embodiment of the present invention will be described in greater detail with reference to FIGS. 13-14.

The implant 214 of FIG. 11 is similar to the embodiments of FIG. 10 except for the protrusions or barbs 218 at one end of implant 214 that extend outwardly from the body of the implant to improve retention with the nerve end.

Although the method discussed above is shown using the embodiment of FIGS. 1 and 3, this method may be practiced similarly with the embodiments of FIGS. 10 and 11. However, referring to FIG. 12, when implant 207 is forced longitudinally into the ends of the severed nerve, the rearward deflection of barbed portions 210 allows implant 207 to be inserted forwardly into the ends of the severed nerve, while the rearward deflection of barbed portions 210 restrains implant 207 from moving rearwardly, thus holding the implant in place.

Figure 13:
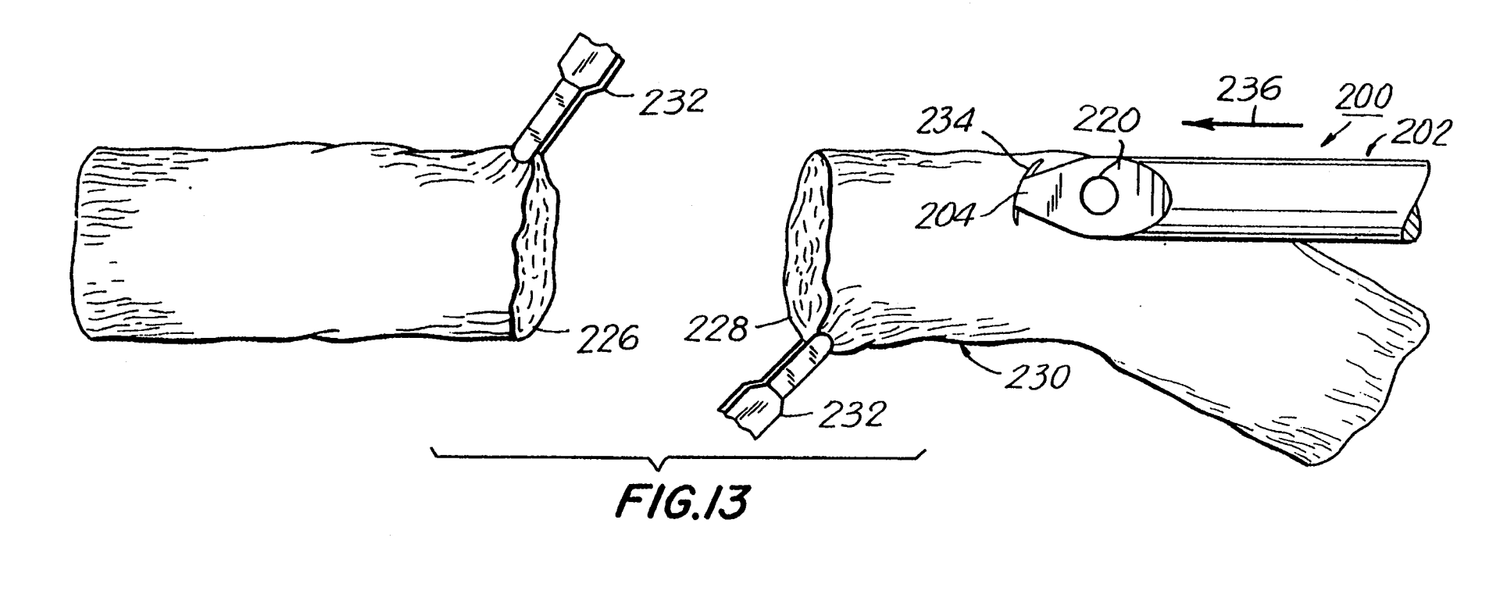
FIGS. 13 and 14 are side perspective views showing the reapproximation and repair of severed nerve ends using the nerve repair device of FIG. 10.
Figure 14:
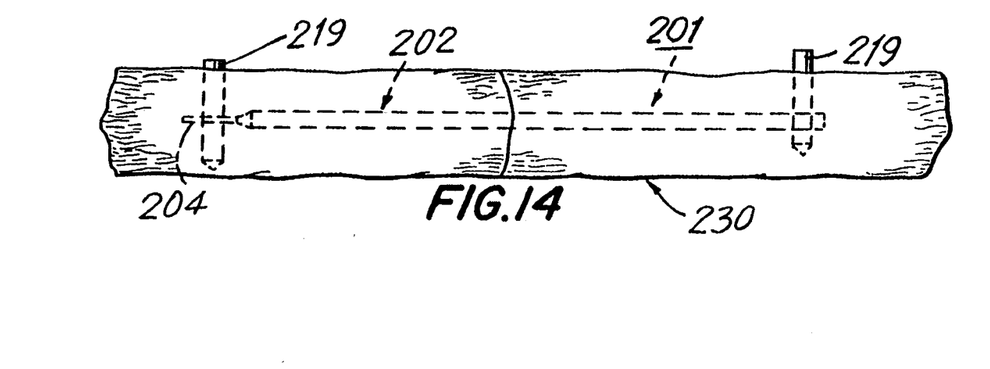

FIGS. 13-14 show another preferred method of nerve repair wherein ends 226, 228 of severed nerve 230 are pulled laterally apart by the use of an appropriate surgical instrument such as forceps 232. Sharpened end 204 of implant 202 is inserted through a site 234 in the perineurium of injured nerve 230 located a suitable distance from the proximal nerve end 228. Sharpened end 204 is insert longitudinally into distal nerve end 226 between the fascicle bundles of the nerve until the severed ends 226, 228 are in close approximation or abutment. Implant 202 is held in place within ends 226, 228 of severed nerve 230 by piercing pins 219 as discussed above. Note that in the embodiment of FIG. 11, as in the embodiment of FIG. 12, when the sharpened end 216 of implant 214 is forced longitudinally into the distal lend of the severed nerve, the rearward deflection of barbed portions 218 allows implant 214 to be inserted forwardly into the ends of the severed nerve, while the rearward deflection of barbed portions 218 helps restrain implant 214 from moving rearwardly within the distal end.

Where the device is fabricated of a resorbable material, such as for example, a copolymer of lactide and glycolide, no subsequent surgery is required for removal after healing of the nerve ends as the implant will be resorbed by the body over a period of time. If the pins are composed of a resorbable material they can optionally remain positioned in the implant. However, if non-resorbable materials are used in constructing the implant and/or pins of the device, the piercing pins are removed from the perineurium and a longitudinal incision may be made through the perineurium along the axis of the nerve, to allow the implant to be withdrawn through the incision.

Figure 9:
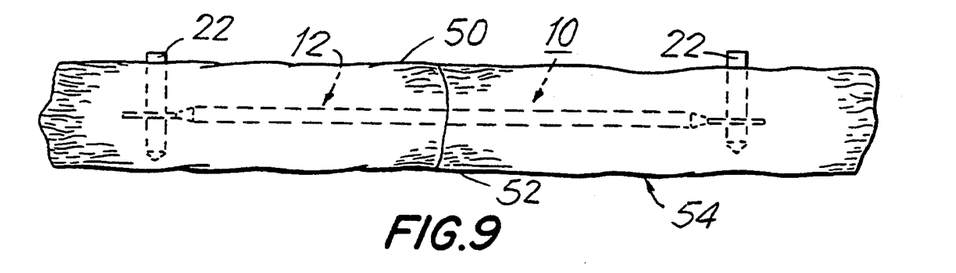
FIG. 9 is a side perspective view of a severed nerve reapproximated and repaired using the nerve repair device of FIG. 1 inserted centrally and longitudinally therein.

Referring to FIGS. 7 and 8, the nerve repair device is shown located longitudinally adjacent the perineurium of the nerve. This location just beneath the nerve sheath advantageously positions the device such that the transverse openings in the device are visible to the surgeon. This facilitates accurate insertion of the piercing pins through the perineurium into the openings. The nerve repair device may also be located longitudinally within the nerve at other suitable locations such as indicated in FIG. 9, wherein nerve repair device 10 is shown located centrally and longitudinally within severed ends 50, 52 of nerve 54.

While the invention hs been particularly shown and described with reference to preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A nerve repair device for repairing severed nerve ends, comprising:
   a substantially solid implant, said implant configured and dimensioned for insertion longitudinally into the severed nerve ends to align them in close approximation;
   anchoring means associated with said implant for holding the severed nerve ends in close approximation; and
   penetration means positioned at opposite end portions of said implant wherein at least one of said penetration means comprises a flattened end portion for penetrating nerve tissue.

2. The repair device of claim 1, wherein said implant is resilient.

3. The repair device of claim 2, wherein said implant is fabricated from a material selected from the group consisting of resorbable materials.

4. The repair device of claim 2, wherein said implant is fabricated from a non-resorbable biocompatible material.

5. The nerve repair device of claim 1 wherein said implant is configured with a substantially rectangular cross section.

6. The nerve repair device of claim 1 wherein said implant is configured with a substantially circular cross section.

7. The repair device of claim 1, wherein said penetration means is integral with said implant.

8. The repair device of claim 7, wherein said penetration means comprises a sharp tip monolithically formed on said implant that extends longitudinally from both ends of said implant.

9. A nerve repair device for repairing severed nerve ends comprising:
   a substantially solid implant having at least one flattened end portion for penetrating nerve tissue, said implant configured and dimensioned for insertion longitudinally into the severed nerve ends to align them in close approximation; and
   anchoring means associated with said implant for holding the severed nerve ends in close approximation, wherein said anchoring means includes a pair of piercing pins.

10. The repair device of claim 9, wherein said anchoring means further includes a pair of openings located in said implant adjacent opposing ends thereof for receiving said pair of piercing pins.

11. The repair device of claim 10, wherein said piercing pins are positioned transverse to said implant.

12. The repair device of claim 11, wherein said implant is of a thickness at least less than the thickness of the severed nerve ends.

13. A nerve repair device for repairing severed nerve ends, comprising:
   an implant configured and dimensioned for insertion longitudinally into end portions of the severed nerve ends to align the severed nerve ends in close approximation; and
   anchoring means associated with said implant for holding the severed nerve ends in close approximation, wherein said anchoring means includes at least one barbed portion adjacent an end portion of said implant, said barbed portion being formed integrally with said implant.

14. A nerve repair device for repairing severed nerve ends, comprising:
   a substantially solid implant having at least one flattened end portion for penetrating nerve tissue, said implant configured and dimensioned for insertion longitudinally into the severed nerve ends to align them in close approximation; and
   anchoring means associated with said implant for holding; the severed nerve ends in close approximation, wherein said anchoring means includes a tip portion flaring symmetrically outward from said implant for engaging with the interior of said nerve.

15. A nerve repair device for repairing severed nerve ends, comprising:
   a resilient elongated implant, said implant having a tip extending generally longitudinally from each end thereof, said tips being configured and adapted to facilitate insertion of said implant generally longitudinally into the interior of the opposed severed end portions of the nerve to align the severed nerve ends in close approximation, said implant having an opening adjacent each tip; and
   a piercing pin extending into each opening for retaining the severed ends of the nerve in close approximation, wherein each tip flares outwardly from said implant for engaging with the interior of the nerve to aid in holding the severed ends in close approximation.

16. A method for holding two severed nerve portions in close apposition, said nerve portions having opposed facing surfaces, the method comprising:
   inserting a first end of an elongated member into a facing surface of a first nerve portion;
   inserting a second end of said elongated member into a facing surface of a second nerve portion; and
   anchoring the elongated member to the nerve portions, wherein said anchoring step comprises inserting first and second pins through said first and second ends of said elongated member.

17. The method of claim 16, wherein said pins are positioned substantially perpendicular to said elongated member.

18. The method of claim 16 wherein said elongated member is inserted in position within said first and second nerve portions adjacent the outermost surface of said first and second nerve portions.

19. A method of repairing severed ends of a damaged nerve, comprising the steps of:
   inserting a substantially rigid implant through a site in the perineurium of a proximal portion of the damaged nerve located a predetermined distance from the damaged end;
   passing the implant into the interior of the proximal nerve end;
   passing the implant longitudinally between the fascicle bundles of a distal end of the nerve and into the distal end of the nerve;
   pulling the severed ends of the nerve together into close approximation over the implant sufficiently to engage each other; and
   anchoring the implant to the nerve adjacent the severed ends in a position to retain the end portions of the nerve in close approximation.

20. The method of claim 19, wherein the method further comprises the step of reconnecting the severed ends of the nerve.

21. The method of claim 20, wherein the implant is composed of a resorbable material, and the method further includes leaving the implant in the nerve to be resorbed by the body.

22. The method of claim 21, wherein the step of anchoring the implant comprises the step of inserting a pin transversely through each end portion of the implant.

23. The method of claim 20, wherein the implant is formed of a non-resorbable biocompatible material, and wherein said method further includes the step of incising the reconnected nerve longitudinally along the axis of the nerve after the reconnected nerve has healed to remove the implant.

24. A method of repairing severed ends of a damaged nerve, comprising the steps of:
   inserting an implant which is substantially rigid prior to insertion through a site in the perineurium of a proximal portion of the damaged nerve located a predetermined distance from the damaged end;
   passing the implant into the interior of the proximal nerve end;
   passing the implant longitudinally between the fascicle bundles of a distal end of the nerve and into the distal end of the nerve;
   pulling the severed ends of the nerve together into close approximation over the implant sufficiently to abut each other; and
   anchoring the implant to the nerve adjacent the severed ends in a position to retain the end portions of the nerve in close approximation.

* * * * *